(12) United States Patent
Sharma et al.

(10) Patent No.: US 10,852,551 B1
(45) Date of Patent: Dec. 1, 2020

(54) WAVEFRONT SENSING WITH ELLIPSOIDAL LENSING STRUCTURE

(71) Applicant: Facebook Technologies, LLC, Menlo Park, CA (US)

(72) Inventors: Robin Sharma, Redmond, WA (US); Andrew John Ouderkirk, Redmond, WA (US)

(73) Assignee: Facebook Technologies, LLC, Menlo Park, CA (US)

( * ) Notice: Subject to any disclaimer, the term of this patent is extended or adjusted under 35 U.S.C. 154(b) by 0 days.

(21) Appl. No.: 16/435,129

(22) Filed: Jun. 7, 2019

(51) Int. Cl.
  *G02B 27/01* (2006.01)
  *G02B 27/09* (2006.01)
  *G02C 7/08* (2006.01)
  *H04N 5/225* (2006.01)

(52) U.S. Cl.
  CPC ..... *G02B 27/0172* (2013.01); *G02B 27/0955* (2013.01); *G02C 7/088* (2013.01); *H04N 5/2253* (2013.01); *H04N 5/2254* (2013.01); *G02B 2027/0178* (2013.01)

(58) Field of Classification Search
  None
  See application file for complete search history.

(56) References Cited

U.S. PATENT DOCUMENTS

| | | | |
|---|---|---|---|
| 2016/0041384 A1* | 2/2016 | Robbins | G02B 27/017 345/156 |
| 2017/0039904 A1* | 2/2017 | Jepsen | G02F 1/13336 |
| 2017/0255020 A1* | 9/2017 | Tam | G02B 27/0172 |

* cited by examiner

*Primary Examiner* — Aneeta Yodichkas
(74) *Attorney, Agent, or Firm* — Freestone Intellectual Property Law PLLC; Aaron J. Visbeek; Andrew J. Cameron

(57) ABSTRACT

An eye is illuminated with infrared illumination light. Illuminating the eye includes illuminating an ellipsoidal lensing structure with the infrared illumination light. A wavefront image of the reflected infrared light is generated. The reflected infrared light is the infrared illumination light reflected by a retina and exiting a pupil of the eye. The ellipsoidal lensing structure redirects the reflected infrared light to a wavefront sensor that generates the wavefront image. An accommodative eye state value is generated based at least in part on the wavefront image.

20 Claims, 14 Drawing Sheets

US 10,852,551 B1

WAVEFRONT SENSING WITH ELLIPSOIDAL LENSING STRUCTURE

TECHNICAL FIELD

This disclosure relates generally to optics, and in particular to wavefront sensing with an ellipsoidal lensing structure.

BACKGROUND INFORMATION

Head mounted displays (HMDs) present virtual images to users of the HMD. In some contexts, it is advantageous for the HMD to determine the location of the eye of the user and/or determine where the eyes of the user are focusing. However, conventional methods for determining where the eye is focusing can be inaccurate, especially across age demographics.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Figure 1:
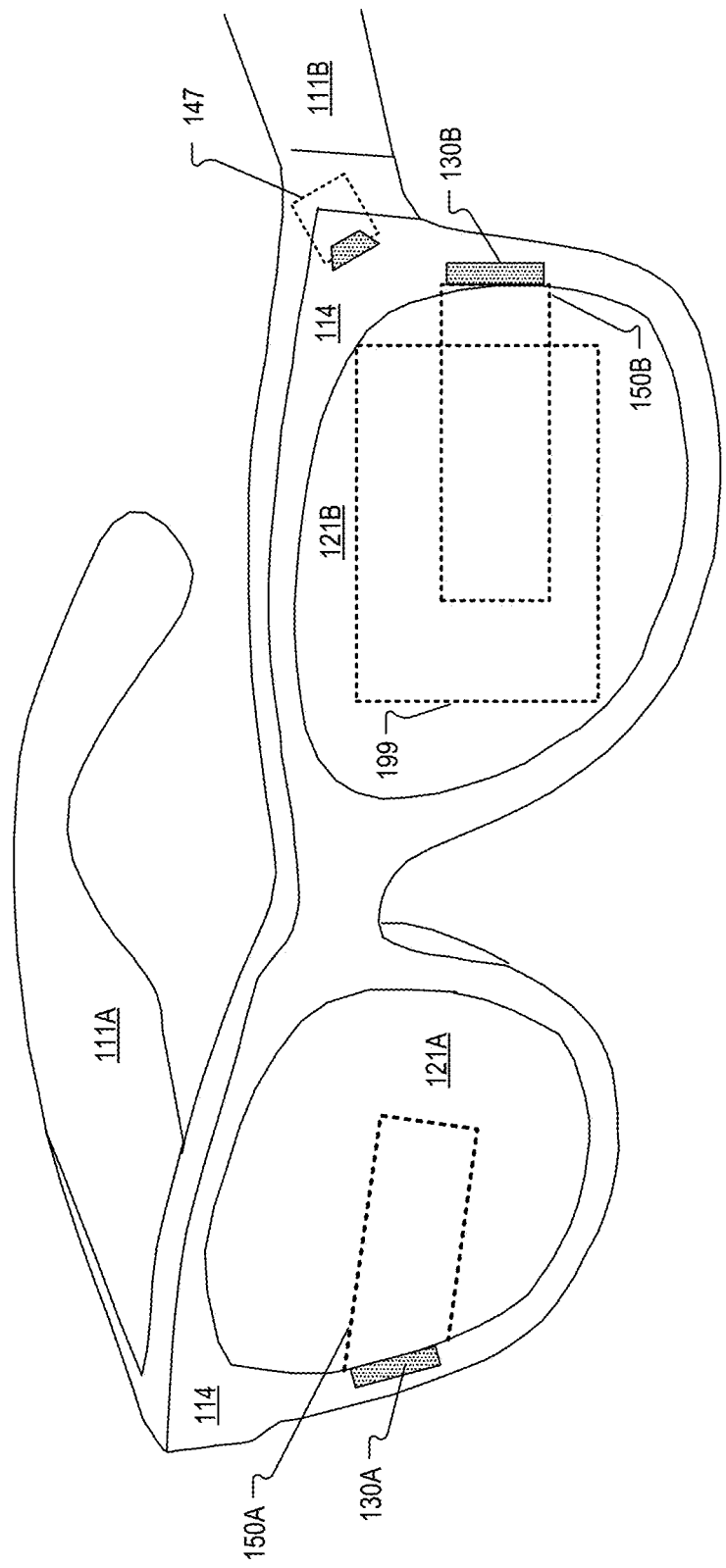
FIG. 1 illustrates an example HMD that may include a combiner for directing light to and from an eye of a user of HMD, in accordance with an embodiment of the disclosure.

Embodiments for wavefront sensing with an ellipsoidal lensing structure are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The apparatus, system, and method for wavefront sensing described in this disclosure are capable of capturing a wavefront image of infrared light propagating through the lens of an eye. By determining the converging or diverging attributes of the wavefront, an accommodative state of the eye can be determined. Conventionally, Vergence-Accommodation Conflict (VAC) is used as a surrogate to approximate the accommodative state of the eye. For example, when two eyes are narrowed the eyes are likely focused to a near-field object (e.g. a book held close) whereas two eyes that are looking straight ahead are likely focused near infinity (e.g. a mountain in the distance). However, VAC only approximates the accommodative state of the eye. Furthermore, the accommodative response of the eye varies over different age groups. For example, individuals under approximately age 45 may accommodate freely while older individuals may have limited accommodation response. For these reasons, it would be advantageous to measure an accommodative state of the eye rather than approximating the accommodative state based on vergence.

Embodiments of the disclosure provide a way to measure an accommodative state of the eye in real time or pseudo real-time. To determine the accommodative state of the eye, an infrared wavefront that has propagated through the lens of the eye is measured by a wavefront sensor. A wavefront image captured by wavefront sensor is analyzed for divergence or convergence to determine the accommodative state of the eye and a virtual image presented to the eye(s) may be adjusted based on the determined accommodative state of the eye. An ellipsoidal combiner is utilized to illuminate the eye with infrared light and to redirect an infrared wavefront (that propagated through the eye lens and is exiting the pupil) to the wavefront sensor. The ellipsoidal combiner is configured so that a center of rotation of an eye of a user of an HMD is positioned at approximately a first foci of the ellipsoidal combiner. The ellipsoidal combiner may include a dichroic coating that passes visible display light or visible scene light from an external environment while reflecting the infrared wavefront. These and other embodiments are described in connection with FIGS. 1-10 below.

FIG. 1 illustrates an example HMD 100 that may include a combiner 199 for directing light to and from an eye of a user of HMD 100, in accordance with an embodiment of the disclosure. Combiner 199 may include an ellipsoidal lensing structure, as will be discussed in more detail below. HMD 100 includes frame 114 coupled to arms 111A and 111B. Lenses 121A and 121B are mounted to frame 114. Lenses 121 may include a prescription matched to a particular wearer of HMD or may be non-prescription lenses. The illustrated HMD 100 is configured to be worn on or about a head of a user of the HMD.

In FIG. 1, each lens 121 includes a waveguide 150 to direct display light generated by a display 130 to an eyebox area for viewing by a wearer of HMD 100. Display 130 may include an LCD, an organic light emitting diode (OLED) display, micro-LED display, quantum dot display, pico-projector, or liquid crystal on silicon (LCOS) display for directing display light to a wearer of HMD 100.

The frame 114 and arms 111 of the HMD 100 may include supporting hardware of HMD 100. HMD 100 may include any of processing logic, wired and/or wireless data interface for sending and receiving data, graphic processors, and one or more memories for storing data and computer-executable instructions. In one embodiment, HMD 100 may be configured to receive wired power. In one embodiment, HMD 100 is configured to be powered by one or more batteries. In one embodiment, HMD 100 may be configured to receive wired data including video data via a wired communication channel. In one embodiment, HMD 100 is configured to receive wireless data including video data via a wireless communication channel.

Lenses 121 may appear transparent to a user to facilitate augmented reality or mixed reality where a user can view scene light from the environment around her while also receiving display light directed to her eye(s) by waveguide(s) 150. Consequently, lenses 121 may be considered (or include) an optical combiner. In some embodiments, display light is only directed into one eye of the wearer of HMD 100. In an embodiment, both displays 130A and 130B are included to direct display light into waveguides 150A and 150B, respectively.

Eye-tracking module 147 may gather eye-tracking data of an eye of the user to determine an eye-position of the eye of the user. In one embodiment, eye-tracking module 147 includes a camera configured to capture infrared images of the eye. The camera may be configured to only capture images of infrared light corresponding to an infrared wavelength of infrared emitters (not illustrated) of HMD 100 that illuminate the eye of the user. Eye-tracking module 147 may be mounted on the inside of the temple of HMD 100. Although eye-tracking module 147 and combiner 199 are illustrated on only one side of HMD 100, they of course may be duplicated on the other side of HMD 100.

Figure 2A:
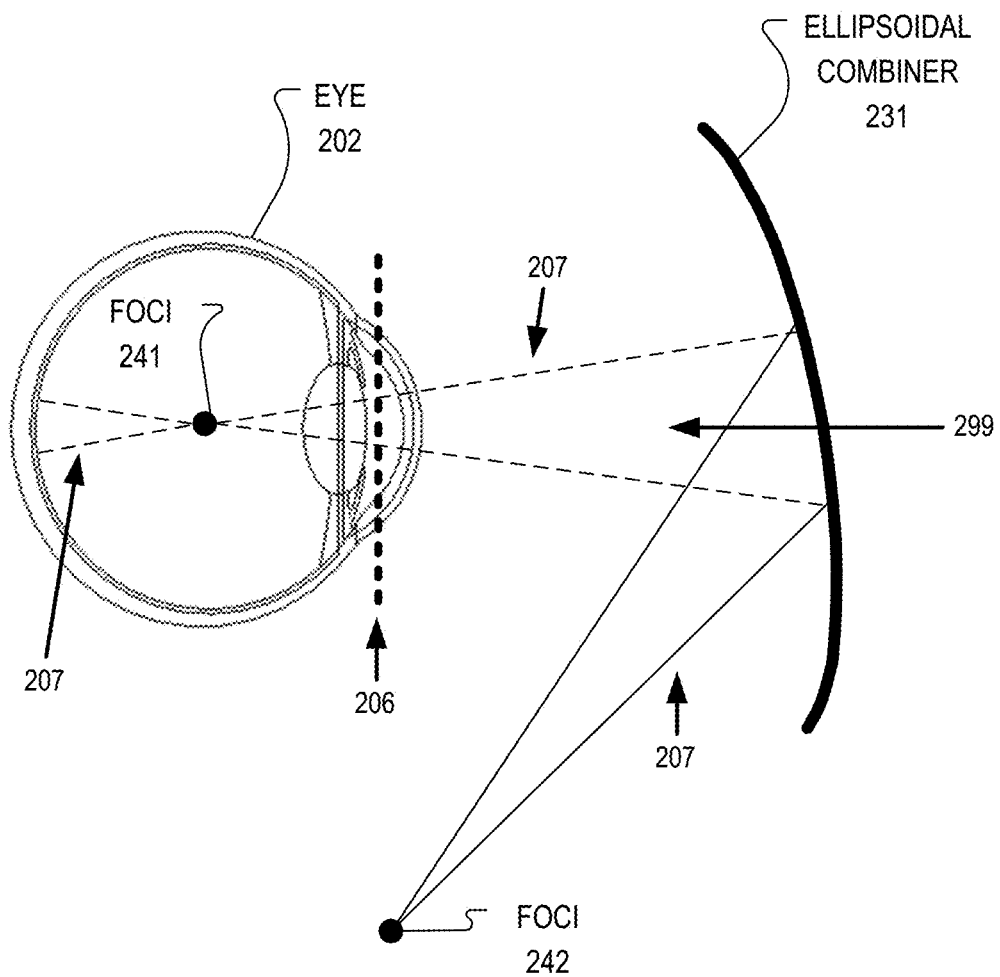
FIGS. 2A-2C illustrate an eye in different positions with respect to an ellipsoidal combiner having an ellipsoidal curvature, in accordance with an embodiment.

FIG. 2A illustrates an ellipsoidal combiner 231 having an ellipsoidal curvature, in accordance with an embodiment of the disclosure. The ellipsoidal curvature of ellipsoidal combiner 231 may follow a three-dimensional curvature defined by a mathematical ellipsoidal equation. In a Cartesian coordinate system, an ellipsoid may be described by:

$$\frac{x^2}{a^2} + \frac{y^2}{b^2} + \frac{z^2}{c^2} = 1 \quad \text{(Equation 1)}$$

where a, b, and c are positive real numbers. Ellipsoidal combiner 231 includes a portion of a full ellipsoid surface. Ellipsoidal combiner 231 may include an infrared reflecting layer disposed on an ellipsoidal curvature so that infrared light encountering the infrared reflecting layer is reflected by the ellipsoidal combiner while visible light is passed. In the context of an HMD, this allows display light or scene light 299 to pass through the infrared reflecting layer (a.k.a. "hot mirror") so that the user of the HMD can view display light or scene light of the external environment. The ellipsoidal combiner 231 is positioned to have a first foci 241 that is at approximately a center of rotation of eye 202. Consequently, light 207 illuminating the ellipsoidal curvature from a second foci 242 of the ellipsoidal combiner 231 will be focused to foci 241 at the center of rotation of eye 202. FIG. 2A illustrates that light 207 propagates through the cornea, anterior chamber, pupil, and lens before becoming incident upon the retina. At least a portion of the illustrated light 207 propagates substantially normal to a two-dimensional pupil plane 206 defined by the pupil of the eye 202.

Figure 2B:
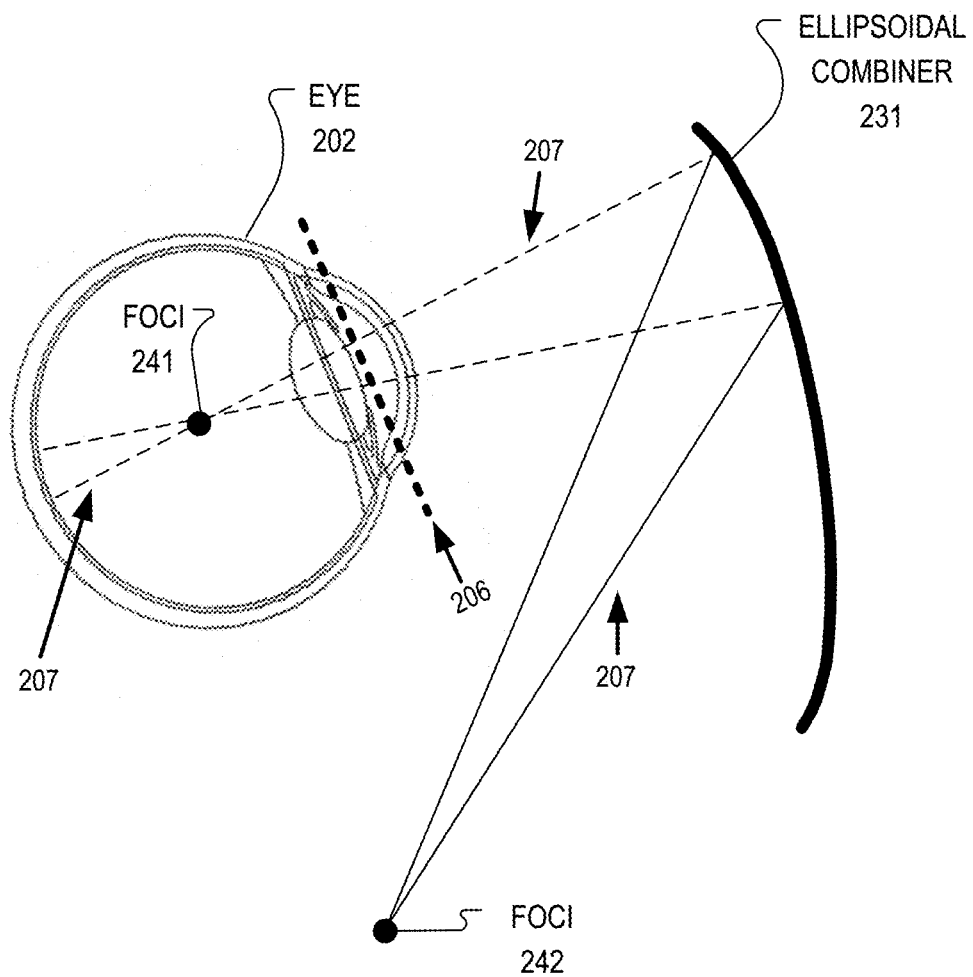

FIG. 2B illustrates ellipsoidal combiner 231 focusing light 207 emitted by second foci 242 to the first foci 241 at the center of rotation of eye 202 when eye 202 has changed a gaze angle of the eye, in accordance with an embodiment of the disclosure. Therefore, a light source positioned at second foci 242 may illuminate a different portion of ellipsoidal combiner 231 when eye 202 rotates and still focus the light 207 to the center of rotation of the eye 202 at the first foci 241 of ellipsoidal combiner 231. The eye 202 illustrated in FIG. 2B may be gazing up or gazing to the left, for example.

Figure 2C:
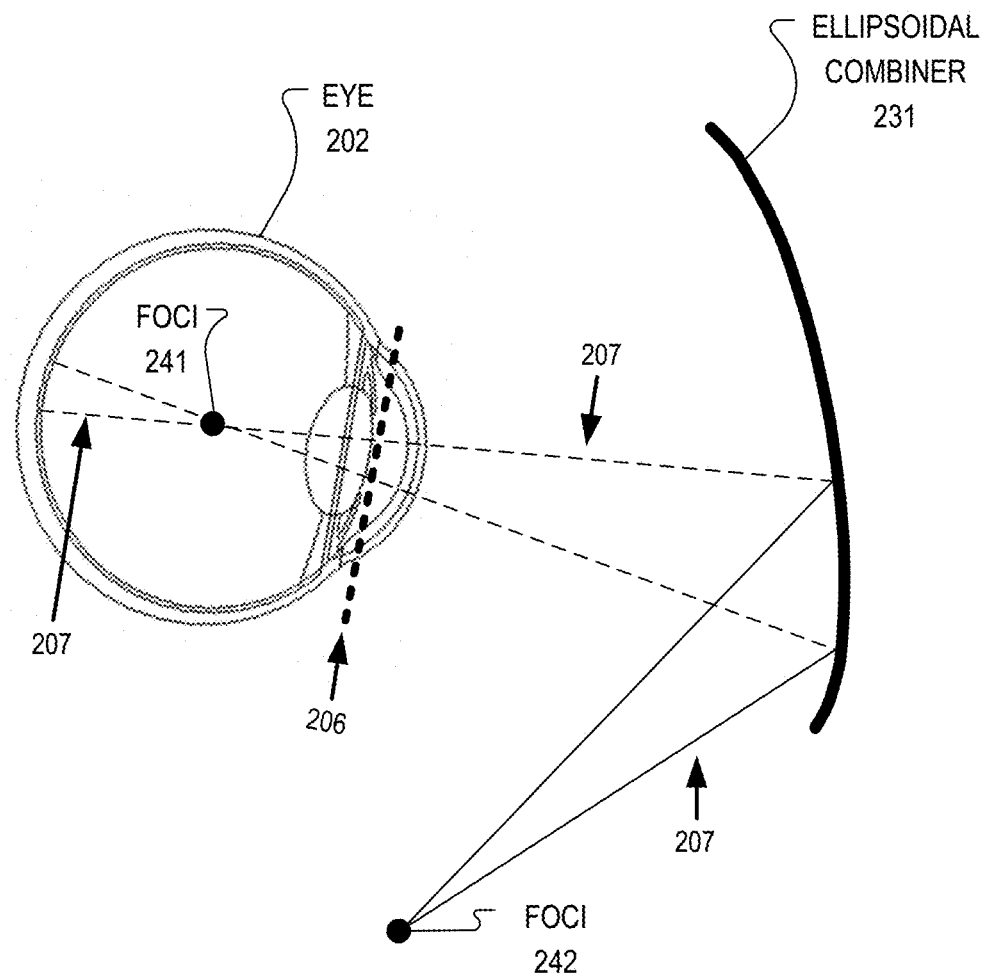

FIG. 2C illustrates ellipsoidal combiner 231 focusing light 207 emitted by second foci 242 to the first foci 241 at the center of rotation of eye 202 when eye 202 is at yet another gaze angle, in accordance with an embodiment of the disclosure. Here again, a light source positioned at second foci 242 may illuminate yet a different portion of ellipsoidal combiner 231 when eye 202 rotates to another gaze angle and still focus the light 207 to the center of rotation of the eye 202 at the first foci 241 of ellipsoidal combiner 231. The eye 202 illustrated in FIG. 2C may be gazing down or gazing to the right, for example. In embodiments of the disclosure, light 207 from second foci 242 may be directed to a particular location of ellipsoidal combiner 231 and redirected by combiner 231 through the pupil to first foci 241 for a range of gaze angles up to 80 degrees horizontal and 80 degrees vertical.

Figure 3A:
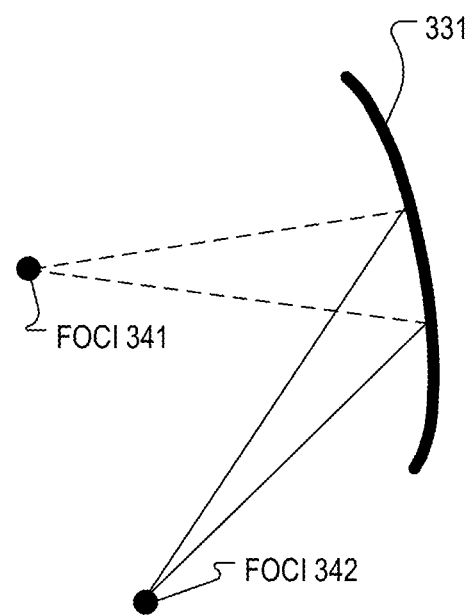
FIG. 3A-3C illustrate example ellipsoidal lensing structures that may be included in an ellipsoidal combiner, in accordance with an embodiment of the disclosure.
Figure 3B:
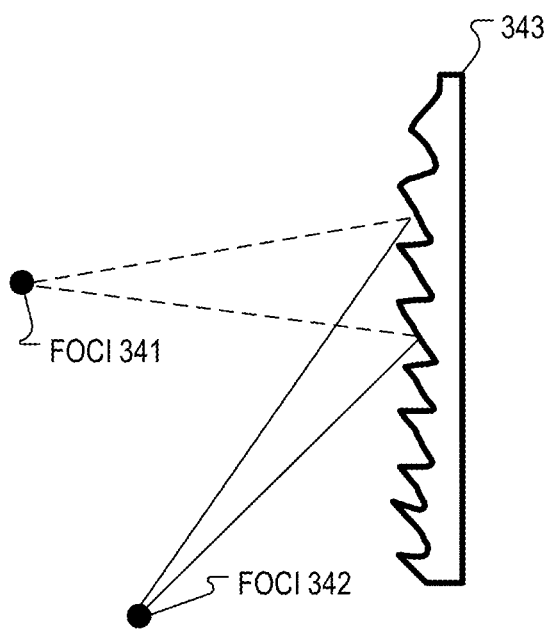
Figure 3C:
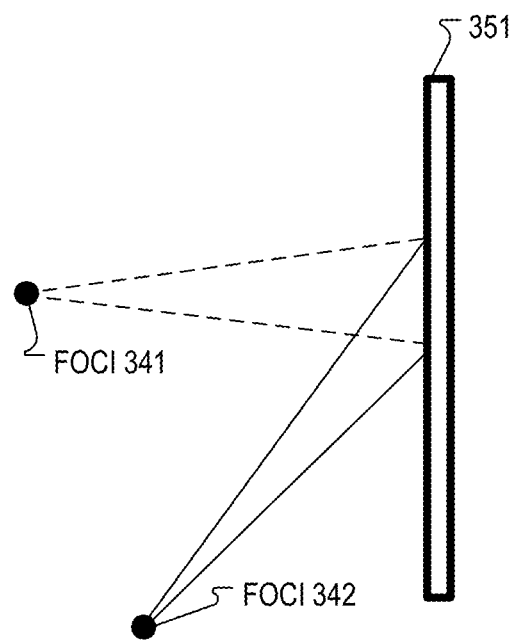

FIGS. 3A-3C illustrate example ellipsoidal lensing structures that may be included in an ellipsoidal combiner such as ellipsoidal combiner 231, in accordance with an embodiment of the disclosure. FIG. 3A illustrates an ellipsoidal lensing structure having a reflecting layer disposed on an ellipsoidal curvature 331. The reflecting layer may be partially reflective (e.g. a beam splitter layer) or be selectively reflective to a particular wavelength or polarization orientation of light to focus light received from second foci 342 to first foci 341. In one embodiment, the reflecting layer is configured to reflect a narrow wavelength band of infrared light centered around 850 nm. In one embodiment, the reflecting layer is configured to pass a first polarization orientation (e.g. s-polarized light) while reflecting a second polarization orientation (e.g. p-polarized light). Including a partially reflective or selectively reflective reflecting layer may allow a combiner to reflect light having particular attributes and pass display light or scene light 299 to the eye of a user.

FIG. 3B illustrates an ellipsoidal Fresnel structure 341 as an example ellipsoidal lensing structure, in accordance with an embodiment of the disclosure. Ellipsoidal Fresnel structure 343 may be an ellipsoidal optical surface decomposed into its Fresnel form having Fresnel facets disposed along a common plane. Hence, ellipsoidal Fresnel structure 343 may function as an ellipsoidal curvature that reflects and focuses light received from second foci 342 to first foci 341, similar to ellipsoidal curvature 331. The partially reflective or selectively reflective layer described in connection with FIG. 3A may be disposed on the Fresnel structure 343.

FIG. 3C illustrates a diffractive ellipsoidal structure 351 as an example ellipsoidal lensing structure, in accordance with an embodiment of the disclosure. Diffractive ellipsoidal structure 351 may include a reflective volume Bragg grating or a holographically recorded ellipsoidal surface that focuses light received from second foci 342 to first foci 341 and is functionally similar to ellipsoidal curvature 331. Since the embodiments illustrated in FIGS. 3B and 3C may be fabricated in a plane, these embodiments may favorably decrease the form factor of the ellipsoidal lensing structure that is selected for a combiner to be included into a lens of a head mounted display.

Figure 4A:
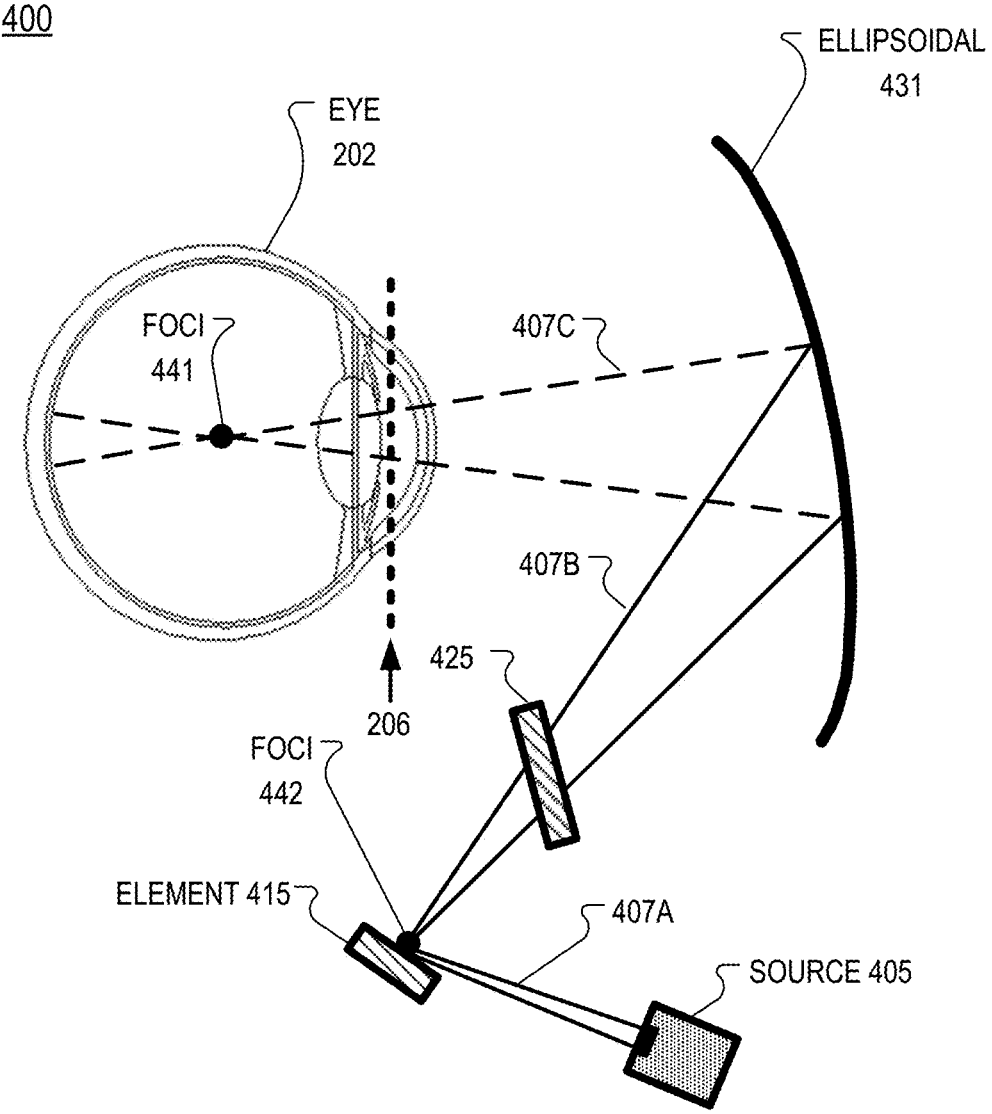
FIG. 4A-4C illustrate a wavefront imaging system including an ellipsoidal lensing structure, in accordance with an embodiment of the disclosure.
Figure 4B:
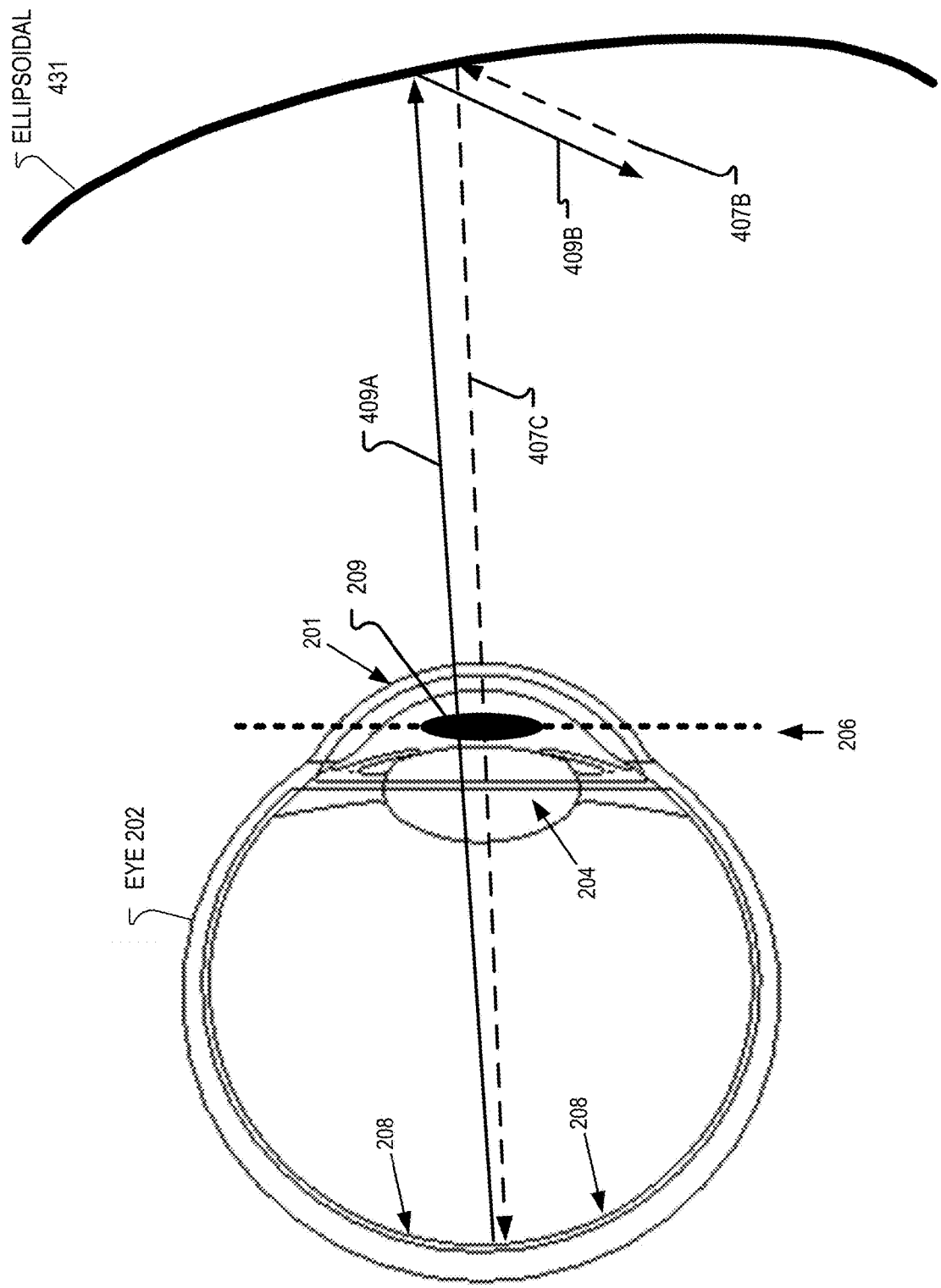
Figure 4C:
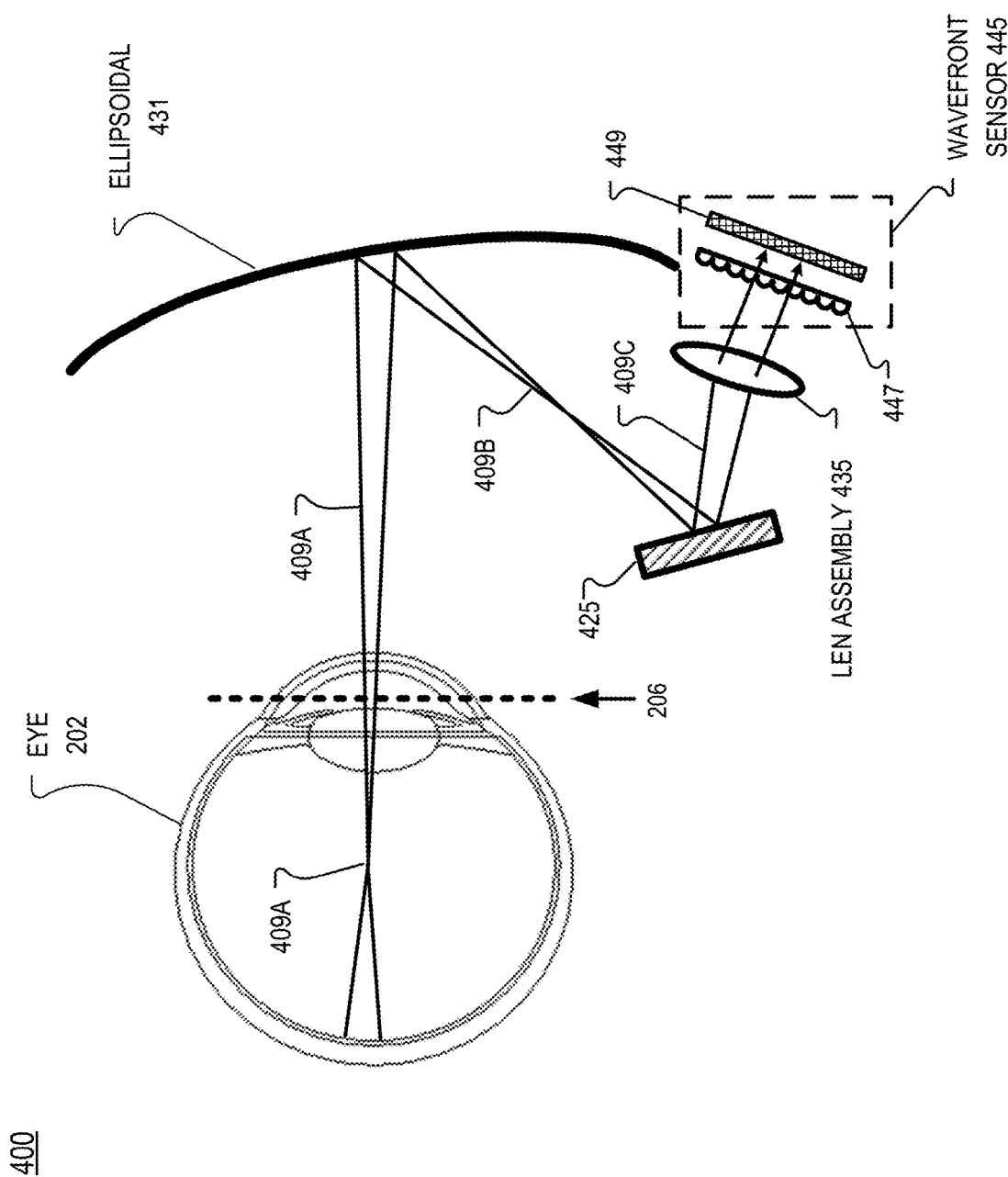

FIGS. 4A-4C illustrate a wavefront imaging system 400 including an ellipsoidal lensing structure, in accordance with an embodiment of the disclosure. FIG. 4A illustrates an illumination portion of system 400. In FIG. 4A, an infrared light source 405 emits infrared illumination light 407A. Infrared light source 405 may include an LED or a laser diode. Infrared illumination light 407A may be collimated light. Light source 405 may be disposed at a second foci 442 of ellipsoidal combiner 431. Beam-steering element 415 is configured to selectively redirect the infrared illumination light 407A to ellipsoidal combiner 431 as infrared illumination light 407B. Ellipsoidal combiner 431 may include any of the ellipsoidal lensing structures 331, 343, or 351. The infrared illumination light 407B that is directed to ellipsoidal combiner 431 may encounter a beam splitter element 425 before encountering ellipsoidal combiner 431. Beam splitter element 425 may pass a portion (e.g. 50%) of infrared illumination light 407B to ellipsoidal combiner 431 while reflecting the remaining portion (e.g. 50%). Ellipsoidal combiner 431 is configured to redirect infrared illumination light 407B to eye 202.

Ellipsoidal combiner 431 is to be positioned such that the first foci 441 of the ellipsoidal combiner 431 is at a center of rotation of eye 202. Beam-steering element 415 may be located at a second foci 442 of ellipsoidal combiner 431. Beam-steering element 415 may be a digital micromirror device (DMD) that adjusts a position of a mirror to direct infrared illumination light 407A to different locations of the ellipsoidal combiner 431. For example, the beam-steering element 415 may be driven to direct infrared illumination light 407B to different positions on ellipsoidal combiner 431 in response to eye-tracking data that includes a position of eye 202. In some embodiments, the DMD includes a curved mirror that acts as a collimator of received infrared illumination light 407A so that infrared illumination light 407B directed toward ellipsoidal combiner 431 is collimated or near-collimated. In another embodiment, a scanning fiber module is used to steer a fiber that carries the infrared illumination light 407A emitted by an infrared light source included in the scanning fiber module. The scanning fiber module may include a one or more piezo-electric actuators that are coupled to move the fiber. The fiber of the scanning fiber module may be moved at a high rate to illuminate different locations of the ellipsoidal combiner 431. The infrared illumination light 407B emitted by the fiber scanning module may be collimated or near-collimated. The output of the fiber may be at the second foci 442 of ellipsoidal combiner 431.

The ellipsoidal combiner 431 redirects infrared illumination light 407B as infrared illumination light 407C. FIG. 4B illustrates a zoomed in view of eye 202 and ellipsoidal combiner 431, in accordance with an embodiment of the disclosure. Portions of infrared illumination light 407C (not illustrated) may not necessarily propagate through the pupil and may be scattered by the iris or cornea. However, at least a portion of infrared illumination light 407C propagates substantially normal to pupil plane 206 of eye 202 and propagates through the cornea 201, anterior chamber, pupil 209, and lens 204 of eye 202 before becoming incident upon the retina 208. A portion (e.g. ~10% for 850 nm light) of infrared illumination light 407C reflects off the retina 208 as reflected infrared light 409A. In FIG. 4B, reflected infrared light 409A propagates through lens 204, pupil 209, and cornea 201 to exit eye 202. Reflected infrared light 409A then encounters ellipsoidal combiner 431 and ellipsoidal combiner 431 redirects the reflected infrared light 409A as reflected infrared light 409B.

FIG. 4C illustrates an imaging portion of system 400 configured to capture a wavefront image of the wavefront formed by reflected infrared light 409. Ellipsoidal combiner 431 directs reflected infrared light 409A to wavefront sensor 445 via beam splitter 425, in the illustrated embodiment. Wavefront sensor 445 is configured to receive the reflected infrared light 409C that is reflected by element 425. Because the pupil of eye 202 acts as a field stop for both infrared illumination light 407C and reflected infrared light 409A, only the infrared illumination light 407C that propagates substantially normal to pupil plane 206 will propagate through the pupil, reflect off the retina, and exit the pupil (also propagating substantially normal to pupil plane 206) to then be redirected to wavefront sensor 445 by ellipsoidal combiner 431. Some portions of infrared illumination light 407C that propagates through the pupil (but does not propagate substantially normal to pupil plane 206) will reflect of retina 208 but the angle of reflection will not allow the reflected infrared light to exit the pupil 209 and it is instead absorbed by other tissue within the eye.

The illustrated embodiment includes a lens assembly 435 to focus the reflected infrared light 409C to wavefront sensor 445. In the illustrated embodiment, wavefront sensor 445 includes a lenslet array 447 disposed over an image sensor 449. The lenslet array 447 is disposed between beam splitter 425 and the image sensor 449. Lenslet array 447 is positioned at a plane that is conjugate to pupil plane 206 of eye 202, in some embodiments. Lenslet array 447 may include a plurality of microlenses that focus reflected infrared light 409C onto image sensor 449 as beam spots. Each microlens may focus a corresponding beam spot onto image sensor 449. When reflected infrared light 409C is a collimated wavefront, the beam spots on image sensor 449 may be axially aligned with an optical axis of its corresponding microlens that focuses that particular beam spot. When reflected infrared light 409C is a diverging wavefront, the beam spots generated by the microlenses will diverge and when reflected infrared light 409C is a converging wavefront, the beam spots generated by the microlenses will converge. Since reflected infrared light 409C propagated through the lens of the eye as reflected infrared light 409A, the wavefront image of reflected infrared light 409C indicates the accommodative state of the eye 202, as will be discussed in more detail below.

In some embodiments, system 400 may include processing logic (not illustrated) that is configured to select a scanning position of beam-steering element 415 and also configured to initiate an image capture of wavefront sensor 445. The scanning position of beam-steering element 415 may change based on eye position data received in eye-tracking data received from an eye-tracking module.

Figure 10:
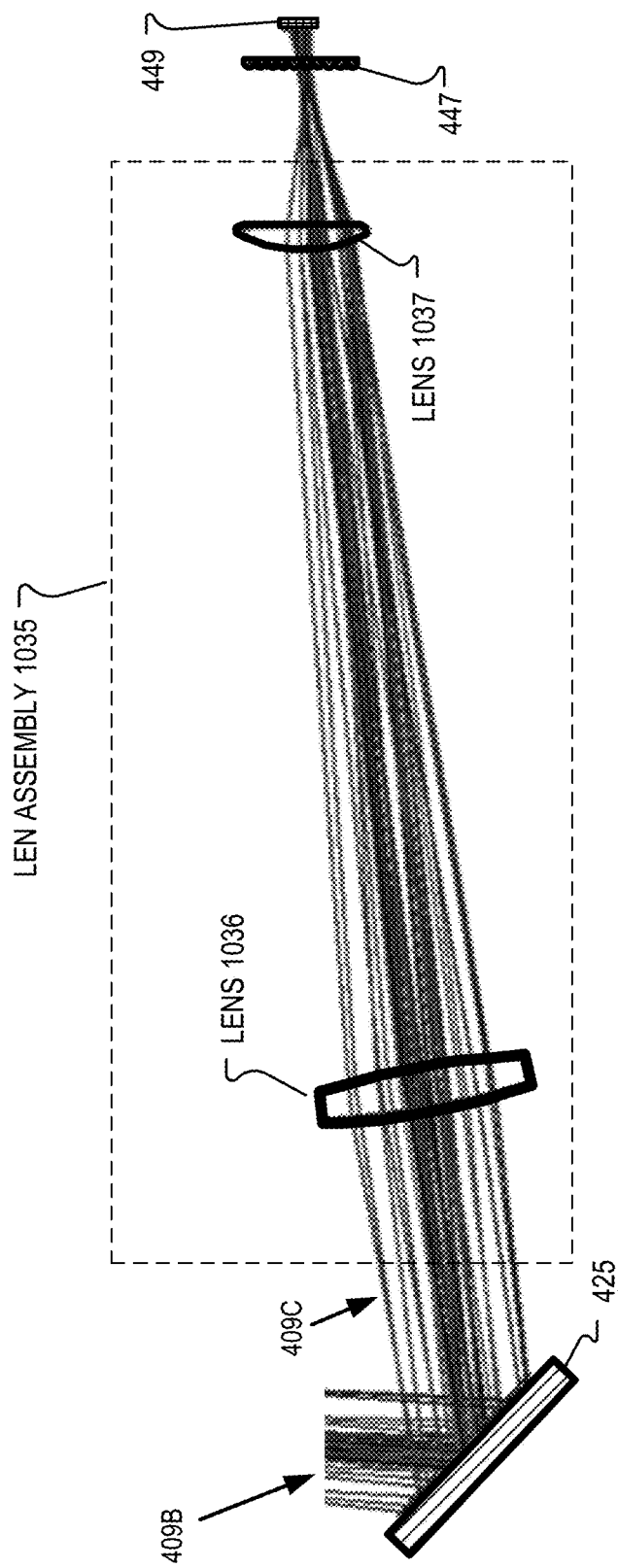
FIG. 10 illustrates an example lens assembly, in accordance with an embodiment of the disclosure.

FIG. 10 illustrates an example lens assembly 1035 that may be used as lens assembly 435, in accordance with an embodiment of the disclosure. In FIG. 10, at least a portion of reflected infrared light 409B received from ellipsoidal combiner 431 is reflected by beam splitter 425. Lens assembly 1035 includes a first focusing lens 1036 and a second focusing lens 537. In FIG. 10, lens 1036 is a double convex lens and lens 1037 is a plano-convex lens. Of course, other lenses may be utilized to focus reflected infrared light 409C onto wavefront sensor 445, depending on the mechanical configuration of the system. In the illustrated embodiment, reflected infrared light 409C encounters lens 1036, lens 1037, lenslet array 447, and image sensor 449, in that order. Lens assembly 1035 focuses reflected infrared light 409C onto wavefront sensor 445.

Figure 5:
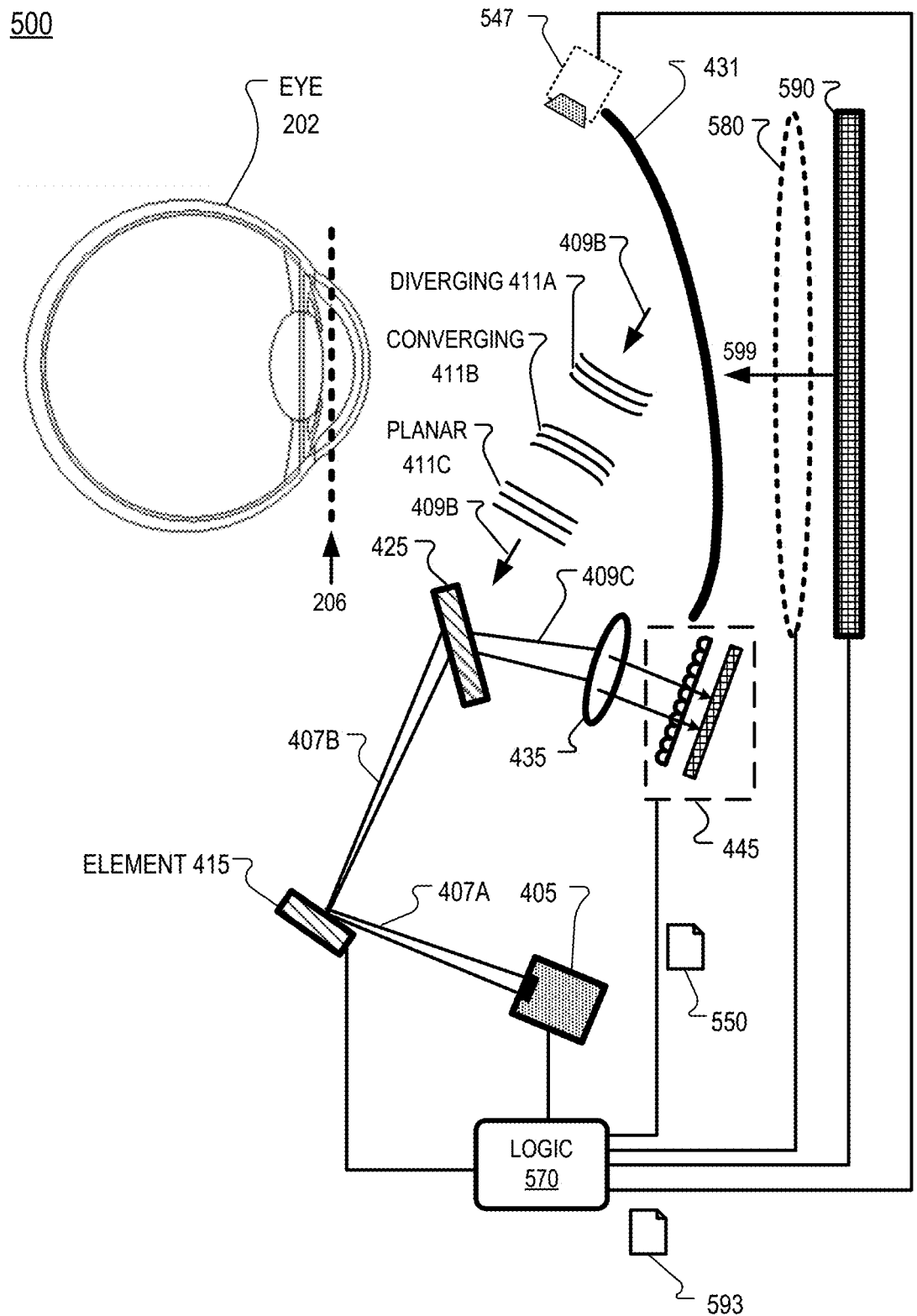
FIG. 5 illustrates a wavefront imaging system that may be utilized in an HMD, in accordance with an embodiment of the disclosure.

FIG. 5 illustrates a wavefront imaging system 500 that may be utilized in an HMD, in accordance with an embodiment of the disclosure. Wavefront imaging system 500 includes an eye-tracking module 547 for determining a position of eye 202. In some embodiments, eye-tracking module 547 includes a camera configured to capture infrared images of eye 202. Eye-tracking module 547 may be configured similarly to eye-tracking module 147. Eye-tracking module 547 generates eye-tracking data 593 that may include a position of eye 202. For example, eye 202 may change gaze angles in any combination of up, down, right, and left, and eye-tracking module 547 may provide those gaze angles in eye-tracking data 593 by analyzing images of eye 202. Display 590 generates visible display light 599 for presenting a virtual image to a user of an HMD. Visible display light 599 may propagate through ellipsoidal combiner 431 with very little (if any) optical loss since ellipsoidal combiner 431 is configured to pass visible light and reflect a particular bandwidth of infrared light emitted by light source 405. Display 590 may include an OLED, micro-LED, or LCD in a virtual reality context. In an augmented reality or mixed reality context, display 590 may include a transparent OLED or an LCOS projector paired with a waveguide included in a lens of an HMD, for example.

In FIG. 5, processing logic 570 is configured to control display 590 and drive images onto display 590. Processing logic 570 is also configured to receive eye-tracking data 593 generated by eye-tracking module 547. Optionally, processing logic 570 is configured to control the intensity of infrared illumination light 407 emitted by light source 405. Processing logic 570 is further configured to select a scanning position of beam-steering element 415 and configured to initiate an image capture of wavefront sensor 445.

FIG. 5 shows that reflected infrared light 409B may include a diverging wavefront 411A, a converging wavefront 411B, or a planar wavefront 411C. The wavefront is directed to wavefront sensor 445 via reflecting element 425 so that wavefront sensor 445 can capture a wavefront image 550 that may be provided to processing logic 570. Although the optical paths associated with infrared illumination light 407C and reflected infrared light 409A/B are not illustrated in FIG. 5, they may follow the optical paths illustrated in FIGS. 4A-4C.

FIG. 5 shows that wavefront imaging system 500 may optionally include a dynamic lens (e.g. a liquid lens) that can be driven to adjust an optical power of the dynamic lens 580 based on the wavefront image 550. Processing logic 570 is configured to adjust an optical power of dynamic lens 580, in the illustrated example of FIG. 5. Since the accommodative state of the eye can be derived from wavefront image 550, a user's refractive error can be measured and corrected for. Display images may need to be tailored to correct for the user's refractive error. Processing logic 570 may receive wavefront image 550 and adjust an optical power of dynamic lens 580 based on the wavefront image to correct for a spherical myopia of a user.

Figure 6:
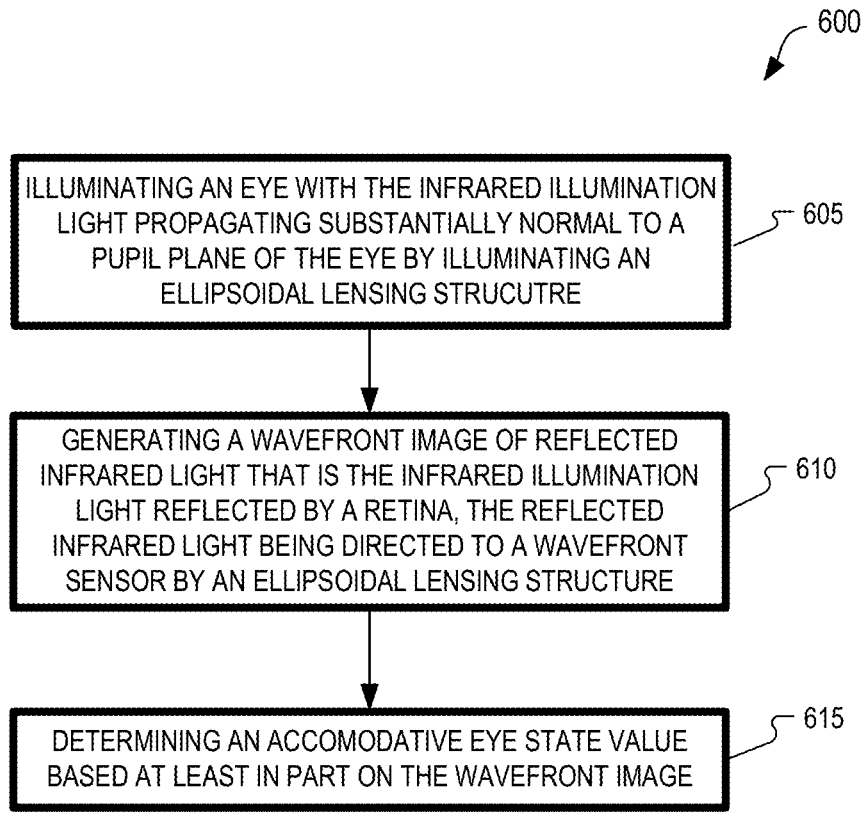
FIG. 6 illustrates a flow chart for a process of generating a retinal image with an ellipsoidal lensing structure, in accordance with an embodiment of the disclosure.

FIG. 6 illustrates a flow chart for a process 600 of generating a retinal image with an ellipsoidal lensing structure, in accordance with an embodiment of the disclosure. The order in which some or all of the process blocks appear in process 600 should not be deemed limiting. Rather, one of ordinary skill in the art having the benefit of the present disclosure will understand that some of the process blocks may be executed in a variety of orders not illustrated, or even in parallel. In some embodiments, all or a portion of the process blocks associated with process 600 are executed by processing logic 570 of FIG. 5.

In process block 605, an eye is illuminated by infrared illumination light (e.g. infrared illumination light 407A) that propagates substantially normal to a pupil plane (e.g. 206) of the eye. Illuminating the eye includes illuminating an ellipsoidal lensing structure (e.g. ellipsoidal lensing structure 331, 343, or 351). The ellipsoidal lensing structure may be configured to have a first foci approximately at a center of rotation of the eye. The infrared illumination light illuminating the ellipsoidal lensing structure may be collimated or near-collimated. The infrared illumination light may be generated by an infrared light source (e.g. light source 405). The infrared illumination light bay be directed to the ellipsoidal lensing structure from a second foci of the ellipsoidal lensing structure. The infrared illumination light may have a wavelength of 850 nm or 940 nm, for example. Processing logic 570 may activate the infrared light source (e.g. light source 405) in some embodiments.

In process block 610, a wavefront image (e.g. 550) of reflected infrared light is generated. The reflected infrared light (e.g. reflected infrared light 409) is the infrared illumination light that is reflected by the retina and exiting a pupil of the eye. The ellipsoidal lensing structure redirects the reflected infrared light to a wavefront sensor (e.g. 445) that generates the wavefront image.

In process block 615, an accommodative eye state value is determined based at least in part on the wavefront image captured by the wavefront sensor. Determining the accommodative eye state value may include analyzing a spacing of beam spots of the wavefront image generated by microlenses of lenslet array focusing the reflected infrared light onto an image sensor.

In an embodiment of process 600, a condensing of the beam spots (the beam spots moving closer together) from the respective microlenses represents a higher accommodation state of the eye and an expansion of the beam spots from the respective microlenses represents a lower accommodative eye state value. The higher accommodative eye state value corresponds to converging optical power of a lens system of the eye and the lower accommodative eye state value corresponds to a diverging optical power of the lens system of the eye. As the beam spots move closer together, it is indicative of the eye focusing at a nearer distance. As the beam spots move farther out (expand), it is indicative of the eye focusing at a farther distance.

Figure 7:
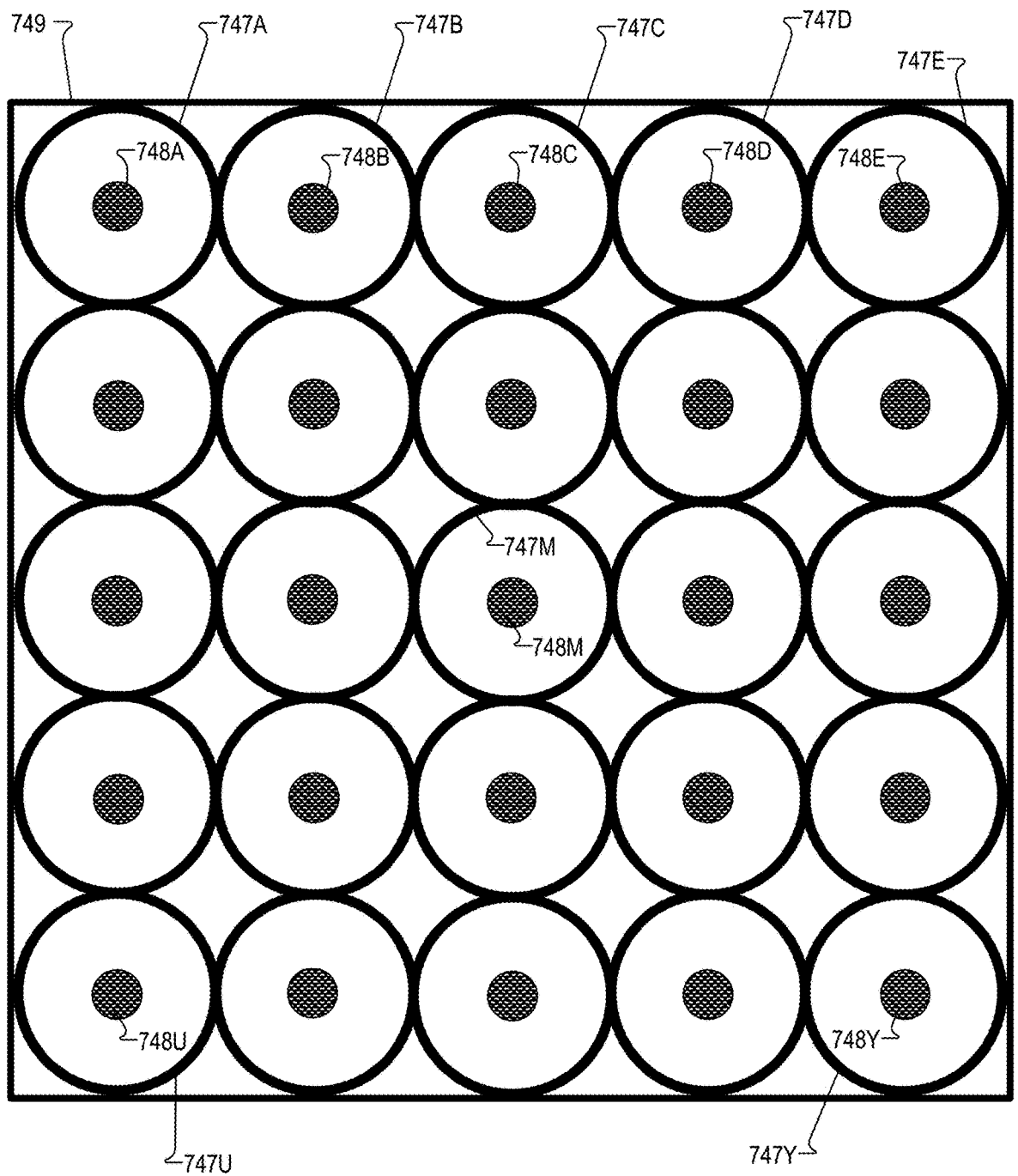
FIG. 7 is a block diagram illustration of a lenslet array focusing a planar wavefront of reflected infrared light onto an image sensor as beam spots, in accordance with an embodiment of the disclosure.

FIG. 7 illustrates a block diagram illustration of a lenslet array 747 focusing a planar wavefront of reflected infrared light 409C onto an image sensor 749 as beam spots 748, in accordance with an embodiment of the disclosure. In the illustrated block diagram example, lenslet array 747 includes a plurality of microlenses 747A-747Y that focus corresponding beam spots 748A-748Y. For example, microlens 747A focuses infrared light onto image sensor 749 as beam spot 748A, microlens 747B focuses infrared light onto image sensor 749 as beam spot 748B . . . and microlens 747Y focuses infrared light onto image sensor 749 as beam spot 748Y. Microlens 747M is the middle microlens in the example 5×5 array of microlenses in lenslet array 747. FIG. 7 illustrates that when reflected infrared light 409C is a planar wavefront (e.g. wavefront 411C), each beam spot 748 is axially aligned with an optical axis of its corresponding microlens that focuses that particular beam spot 748.

Accordingly, each beam spot 748 in the example is equidistant. In other examples, beam spots 748 may not necessarily be equidistance for incoming planar wavefronts.

Figure 8:
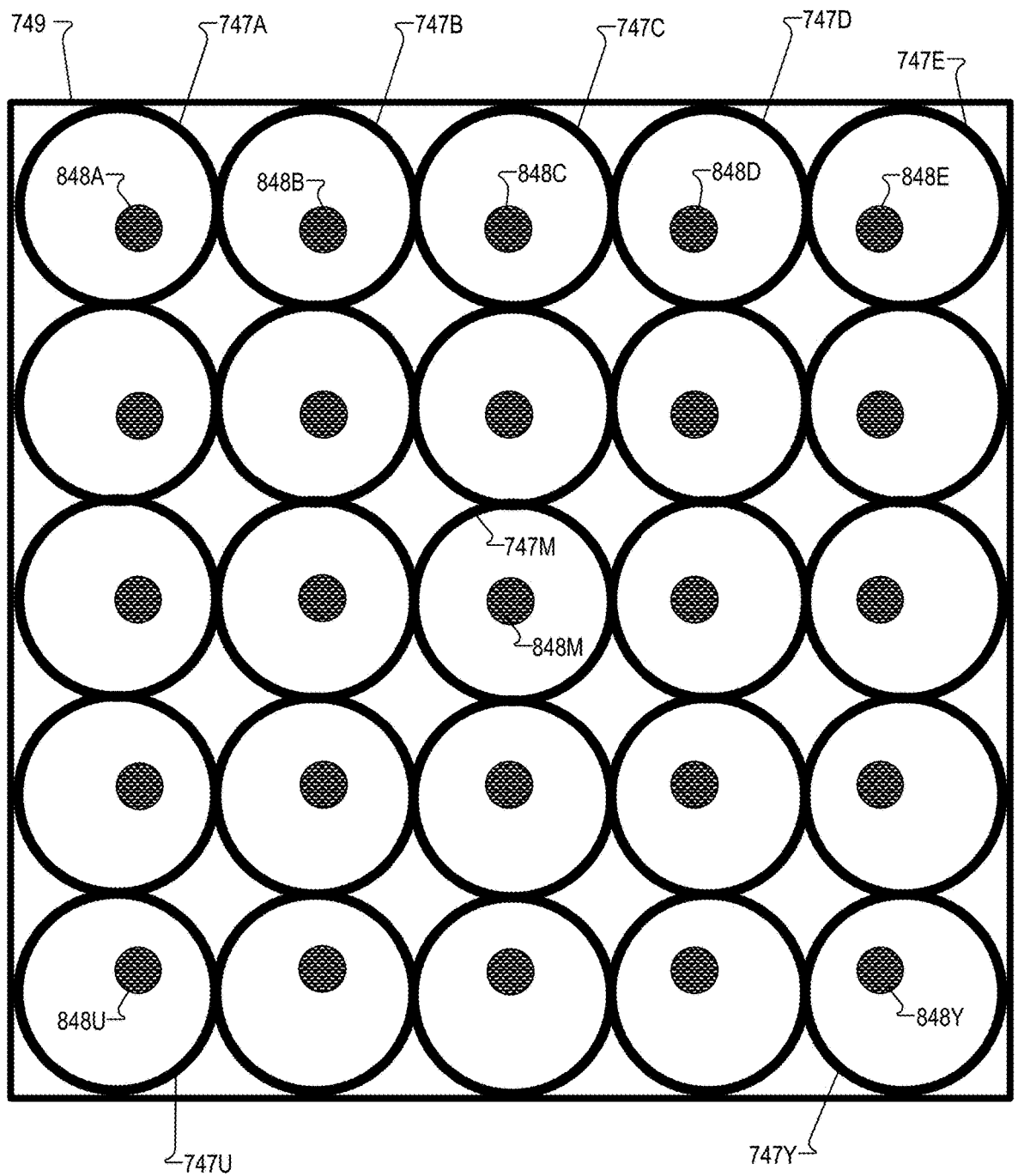
FIG. 8 is a block diagram illustration of a lenslet array focusing a converging wavefront of reflected infrared light onto an image sensor as beam spots, in accordance with an embodiment of the disclosure.

FIG. 8 illustrates a block diagram illustration of a lenslet array 747 focusing a converging wavefront of reflected infrared light 409C onto an image sensor 749 as beam spots 848, in accordance with an embodiment of the disclosure. FIG. 8 illustrates that when reflected infrared light 409C is a converging wavefront (e.g. wavefront 411B), beam spots 848 have converged toward middle beam spot 848M. Accordingly, when the beam spots 848 are converging, a wavefront image that captures beam spots 848 will indicate that the lens system of eye 202 is focusing at nearer distances. The closer the beam spots 848 converge, the nearer the distance the eye 202 may be focusing to.

Figure 9:
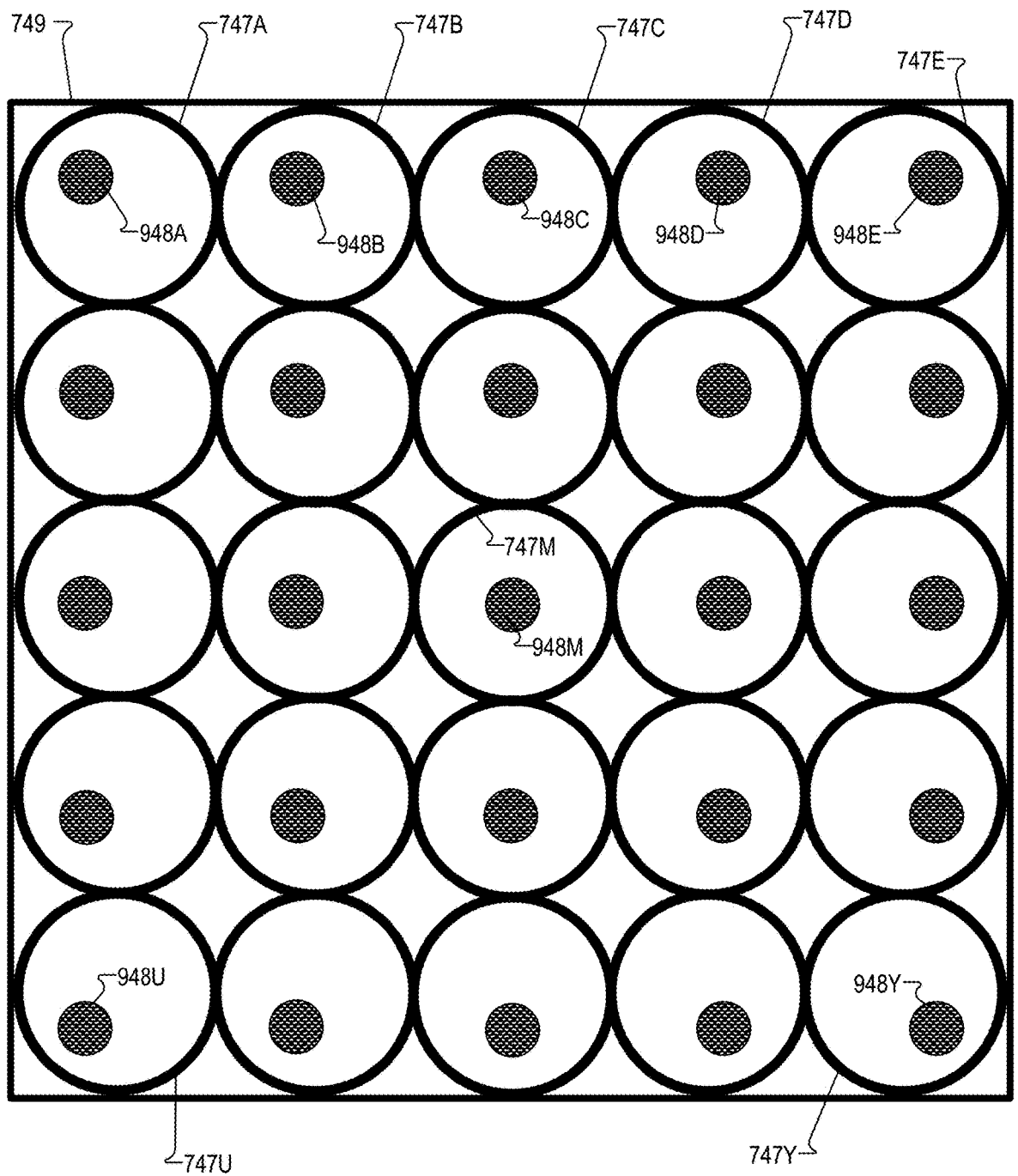
FIG. 9 is a block diagram illustration of a lenslet array focusing a diverging wavefront of reflected infrared light onto an image sensor as beam spots, accordance with an embodiment of the disclosure.

FIG. 9 illustrates a block diagram illustration of a lenslet array 747 focusing a diverging wavefront of reflected infrared light 409C onto an image sensor 749 as beam spots 948, in accordance with an embodiment of the disclosure. FIG. 9 illustrates that when reflected infrared light 409C is a diverging wavefront (e.g. wavefront 411A), beam spots 848 have diverged away from middle beam spot 948M. Accordingly, when the beam spots 948 are diverging, a wavefront image that captures beam spots 948 will indicate that eye 202 is focusing at a farther distance. In some cases, wavefront 411A is not diverging but merely less divergent than wavefront 411C and the beam spots 948 formed on the wavefront image are also not converging, but rather converging less than beam spots 848 of FIG. 8. In this case, the lesser extent of the convergence of beam spots 948 (compared with the convergence of beam spots 848) indicates that the eye 202 is focusing at a farther distance than the more condensed beam spots 848. Consequently, a greater condensing of the beam spots from the respective microlenses represents a near-focused accommodative eye state value where the eye is focused at a near distance and a lesser condensing of the beam spots from the respective microlenses represents a far-focused accommodative eye state value where the eye is focused at a farther distance.

Although lenslet array 747 or 447 may not be configured exactly as illustrated in FIGS. 7-9 in all implementations, FIGS. 7-9 illustrate how analysis of the positioning of the beam spots will indicate the diverging or converging nature of the wavefront of reflected infrared light 409C as well as the magnitude of the divergence or convergence. Accordingly, a magnitude and nature of the accommodative state of the lens system of eye 202 may be determined from a wavefront image generated by wavefront sensor 445 by analyzing the spacing of the beam spots.

Returning to FIG. 6, the ellipsoidal lensing structure may be included in a near-eye combiner that is substantially transparent to visible light and the near-eye combiner and the wavefront sensor may be included in an HMD, such as HMD 100. Process 600 may further include adjusting a virtual image presented to an eye by the HMD in response to the accommodative eye state value. Adjusting the virtual image may include applying blurring filters to provide focusing cues for the user or moving virtual objects in the virtual image, for example. In an example, the determined accommodative eye state value is used to identify a virtual object in a virtual image that the user is focused on. A gaze angle of the eye may also be used to determine the virtual object in a virtual image that a user is focused on. Portions of the virtual image that are not at the same focus distance as the virtual object the user is focused on may be blurred to enhance the user's ability to focus on the virtual object, for example.

Embodiments of the invention may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The term "processing logic" (e.g. 670, 870 or 970) in this disclosure may include one or more processors, microprocessors, multi-core processors, Application-specific integrated circuits (ASIC), graphics processing units (GPUs), and/or Field Programmable Gate Arrays (FPGAs) to execute operations disclosed herein. In some embodiments, memories (not illustrated) are integrated into the processing logic to store instructions to execute operations and/or store data. Processing logic may also include analog or digital circuitry to perform the operations in accordance with embodiments of the disclosure.

A "memory" or "memories" described in this disclosure may include one or more volatile or non-volatile memory architectures. The "memory" or "memories" may be removable and non-removable media implemented in any method or technology for storage of information such as computer-readable instructions, data structures, program modules, or other data. Example memory technologies may include RAM, ROM, EEPROM, flash memory, CD-ROM, digital versatile disks (DVD), high-definition multimedia/data storage disks, or other optical storage, magnetic cassettes, magnetic tape, magnetic disk storage or other magnetic storage devices, or any other non-transmission medium that can be used to store information for access by a computing device.

A computing device may include a desktop computer, a laptop computer, a tablet, a phablet, a smartphone, a feature phone, a server computer, or otherwise. A server computer may be located remotely in a data center or be stored locally.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method comprising:
    illuminating an eyebox area with infrared illumination light propagating substantially normal to a pupil plane of an eye, wherein illuminating the eyebox area includes illuminating an ellipsoidal combiner with the infrared illumination light, wherein the ellipsoidal combiner is configured to reflect the infrared illumination light to a first foci located at a center of rotation of the eye, and wherein the ellipsoidal combiner is configured to pass visible light;
    generating a wavefront image of reflected infrared light, wherein the reflected infrared light is the infrared illumination light reflected by a retina and exiting a pupil of the eye, and wherein the ellipsoidal combiner reflects the reflected infrared light to a wavefront sensor that generates the wavefront image; and
    determining an accommodative eye state value based at least in part on the wavefront image.

2. The method of claim 1, wherein the ellipsoidal combiner is configured to have a first foci at a center of rotation of the eye.

3. The method of claim 2, wherein illuminating the ellipsoidal combiner includes directing, from a second foci of the ellipsoidal combiner, the infrared illumination light to the ellipsoidal combiner.

4. The method of claim 1, wherein generating the wavefront image includes receiving the reflected infrared light with the wavefront sensor including an image sensor and a lenslet array.

5. The method of claim 4, wherein the lenslet array is positioned at a plane that is conjugate to a pupil plane of the eye.

6. The method of claim 4, wherein determining the accommodative eye state value includes analyzing a spacing of beam spots of the wavefront image generated by microlenses of the lenslet array focusing the reflected infrared light onto the image sensor.

7. The method of claim 6, wherein a greater condensing of the beam spots from the respective microlenses represents a near-focused accommodative eye state value, and wherein a lesser condensing of the beam spots from the respective microlenses represents a far-focused accommodative eye state value.

8. The method of claim 1, wherein ellipsoidal combiner is included in a near-eye combiner that is substantially transparent to visible light, the near-eye combiner and the wavefront sensor included in a head mounted display (HMD).

9. The method of claim 8 further comprising:
    adjusting a virtual image presented to the eye by the HMD in response to the accommodative eye state value.

10. The method of claim 8 further comprising:
adjusting an optical power of a dynamic lens in response to the accommodative eye state value, wherein the dynamic lens is positioned to impart optical power to display light emitted by a display of the HMD.

11. A near-eye optical system comprising:
    an infrared light source configured to emit infrared illumination light;
    an ellipsoidal combiner configured to reflect the infrared illumination light to an eyebox area, the ellipsoidal combiner including an ellipsoidal lensing structure having a first foci and a second foci, wherein the ellipsoidal combiner is configured to be positioned near an eyebox area where the first foci of the ellipsoidal lensing structure would be located approximately at a center of rotation of an eye placed in the eyebox area, and wherein the ellipsoidal combiner is configured to pass visible light;
    a beam-steering element configured to selectively redirect the infrared illumination light to the ellipsoidal combiner;
    a wavefront sensor; and
    a beam splitter configured to receive infrared retina reflected light from the ellipsoidal combiner and to redirect a portion of the infrared retina reflected light to the wavefront sensor, wherein the infrared illumination light emitted by the infrared light source propagates through the beam splitter prior to being reflected to the eyebox area by the ellipsoidal combiner.

12. The near-eye optical system of claim 11, wherein the wavefront sensor includes:
    an image sensor; and
    a lenslet array disposed between the beam splitter and the image sensor.

13. The near-eye optical system of claim 12, wherein the lenslet array is positioned at a plane that is conjugate to a pupil plane of an eye placed in the eyebox area.

14. The near-eye optical system of claim 11, wherein the infrared light source is disposed at the second foci of the ellipsoidal lensing structure.

15. The near-eye optical system of claim 11, wherein the beam-steering element is disposed at the second foci of the ellipsoidal lensing structure.

16. The near-eye optical system of claim 11, further comprising a focusing lens disposed between the wavefront sensor and the beam splitter.

17. The near-eye optical system of claim 11, wherein the ellipsoidal combiner is substantially transparent to visible light and configured to redirect the infrared illumination light.

18. The near-eye optical system of claim 11, wherein the infrared illumination light emitted by the infrared light source is collimated or near-collimated.

19. A Head Mounted Display (HMD) comprising:
    an infrared light source configured to emit infrared illumination light;
    an ellipsoidal combiner configured to reflect the infrared illumination light to an eyebox area, the ellipsoidal combiner including an ellipsoidal lensing structure having a first foci and a second foci, wherein the ellipsoidal combiner is configured to be positioned near an eyebox area where the first foci of the ellipsoidal lensing structure would be located at approximately a center of rotation of an eye placed in the eyebox area, and wherein the ellipsoidal combiner is configured to pass visible light; and a wavefront sensor configured to receive infrared retina reflected light from the ellipsoidal combiner, wherein the infrared retina reflected light is the infrared illumination light reflected by a retina and exiting a pupil of the eye placed in the eyebox area, and wherein the ellipsoidal combiner reflects the infrared retina reflected light to the wavefront sensor.

20. The HMD of claim 19, wherein the infrared light source is disposed at the second foci of the ellipsoidal lensing structure.

* * * * *